United States Patent [19]

Hubbard et al.

[11] Patent Number: 4,781,525
[45] Date of Patent: Nov. 1, 1988

[54] FLOW MEASUREMENT SYSTEM

[75] Inventors: Lloyd C. Hubbard, Minnetonka; Earl W. Clausen, Wayzata, both of Minn.

[73] Assignee: Minnesota Mining and Manufacturing Company, St. Paul, Minn.

[21] Appl. No.: 74,549

[22] Filed: Jul. 17, 1987

[51] Int. Cl.$^4$ .............................................. F01D 17/02
[52] U.S. Cl. ........................................ 415/30; 415/17; 417/63
[58] Field of Search ............... 415/26, 30, 17; 417/22, 417/63

[56] References Cited

U.S. PATENT DOCUMENTS

| 4,005,581 | 2/1977 | Aanstad | 415/17 |
| 4,496,286 | 1/1985 | Gagnon | 417/22 |
| 4,502,842 | 3/1985 | Currier et al. | 417/63 |
| 4,589,822 | 5/1986 | Clausen et al. | 415/170 A |
| 4,636,144 | 1/1987 | Abe et al. | 417/63 |
| 4,687,410 | 8/1987 | Cline et al. | 415/30 |

Primary Examiner—Robert E. Garrett
Assistant Examiner—John T. Kwon
Attorney, Agent, or Firm—Donald M. Sell; Robert W. Hoke, II

[57] ABSTRACT

Blood flow rate in a motor driven centrifugal blood pump is measured indirectly and non-invasively by sensing a first parameter representative of pump RPM and a second parameter representative of motor torque. The blood flow rate is computed as a function of the first and second parameters. By measuring the second parameter in a zero flow condition while the motor is being driven at a known RPM, a viscosity calibration factor is determined which is used, together with the first and second parameters in the calculation of flow rate.

7 Claims, 2 Drawing Sheets

FLOW MEASUREMENT SYSTEM

BACKGROUND OF THE INVENTION

1. Field of the Invention

The present invention is related to the measurement of blood flow from a centrifugal blood pump.

2. Description of the Prior Art

Centrifugal pumps have been used for many years to pump a wide variety of different fluid materials. In general, a centrifugal pump includes a pumping chamber with an inlet aligned with a rotational axis of the pump, an outlet adjacent the periphery of the pumping chamber and an impeller mounted within the pumping chamber for rotation about an axis. The impeller in such pumps can be mounted on a drive shaft which extends outside the pumping chamber to a rotational drive source, or the shaft can be mounted within the pumping chamber as a spindle about which the impeller rotates (i.e. rotatably driven by means other than the rotation of the shaft, such as a magnet drive arrangement). In either case, as the impeller is rotated, it imparts force and velocity to the fluid, thus pumping the fluid from the pump inlet to the pump outlet.

In recent years, centrifugal pumps have been used extensively for pumping blood. One example of a centrifugal blood pump is shown in our U.S. Pat. No. 4,589,822, which is assigned to the same assignee as the present application.

Because the flow produced by a centrifugal pump may be independent of the speed of rotation (RPM) of the centrifugal pump impeller, in prior art centrifugal blood pump systems, an independent flow measurement device has been used.

There are two centrifugal blood pumps currently available in the United States—one produced by Bio-Medicus and the other by the assignee of the present application. The Bio-Medicus system uses an electromagnetic flowmeter, while the system of the assignee of the present application uses a Doppler ultrasonic flowmeter. Both of these approaches require that an appropriate transducer be placed in or near the blood conduit tubing.

There is a continuing need for improved flow measurement method for use in centrifugal blood pump systems. In particular, there is a need for a flow measurement method which is insensitive to stray electromagnetic radiation (such as from electro-cautery equipment) and which requires no operator-placed transducer.

SUMMARY OF THE INVENTION

The present invention is a method of indirectly and noninvasively measuring blood flow from a motor driven centrifugal pump. The present invention takes advantage of the fact that, at a constant speed of rotation and a constant viscosity, the torque required to drive a centrifugal pump is directly related to the flow produced by the pump. Blood flow is measured by sensing a first parameter which is representative of pump RPM, sensing a second parameter which is representative of motor torque and computing a blood flow rate as a function of the sensed first and second parameters.

In preferred embodiments of the present invention, a viscosity factor representative of the viscosity of the fluid is determined, and the computing of the flow rate is also as a function of the viscosity factor.

The viscosity factor is preferably determined by causing the pump to operate at a selected RPM, clamping an outlet line to reduce the flow to zero, sensing the second parameter representative of motor torque while the flow is zero and the pump is operating, and computing the viscosity factor based upon the value of the second parameter as sensed while blood flow is zero.

DETAILED DESCRIPTION OF THE PREFERRED EMBODIMENTS

Figure 1:
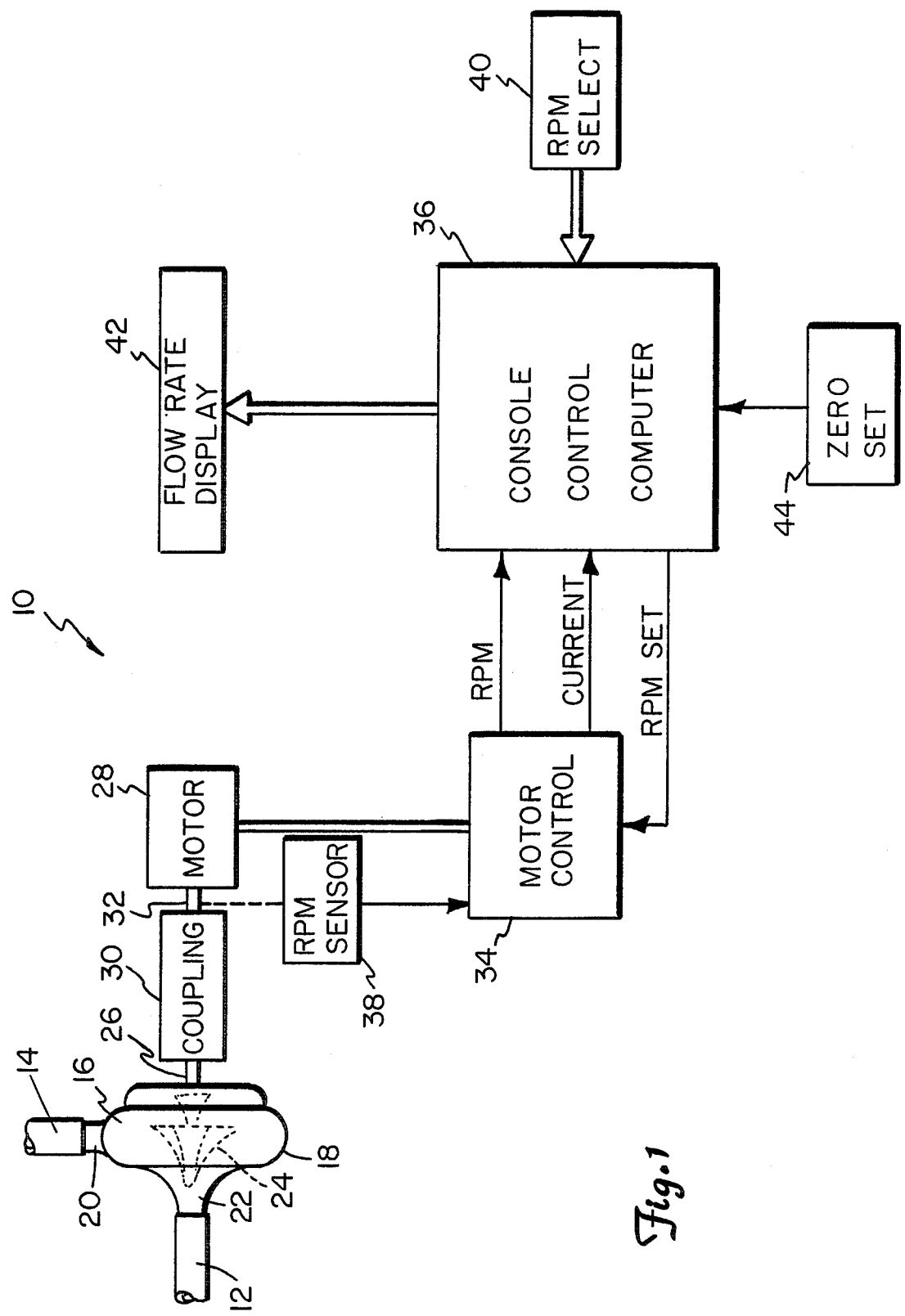
FIG. 1 shows a centrifugal pump system which uses the flow measurement method of the present invention.

Centrifugal blood pump system 10 shown in FIG. 1 is of a type which is typically used in providing life support to a patient (not shown) during open heart surgery or heart assist. System 10 includes an outlet line 12 which supplies blood to the patient and a return line 14 which receives a return flow of blood (either from the patient or from an oxygenator system (not shown)). Centrifugal blood pump 16 includes housing 18, inlet 20, outlet 22, impeller 24, and drive shaft 26. Motor 28 provides rotary drive to drive shaft 26 and thus to impeller 24, through coupling 30. In one embodiment, coupling 30 is a magnetic type coupling, and in other embodiments is a quick connect/disconnect shaft coupling. As motor shaft 32 of motor 28 is rotated, coupling 30 imparts the rotary drive to pump drive shaft 26. This causes impeller 24 to rotate within housing 18.

Motor 28 receives control signals from motor control 34. In a preferred embodiment of the present invention, motor 28 is a permanent magnet DC electric motor and motor control 34 controls current flow to motor 28 to control the speed of rotation (RPM) of motor 28 (and thus of impeller 24).

Motor control 34 controls the drive current to motor 28 as a function of an RPM SET signal which it receives from console control computer 36 (preferably a microcomputer), and an RPM feedback signal which it receives from RPM sensor 38. The RPM SET signal provided by computer 36 is based upon inputs provided by the operator through RPM select inputs 40 (which may be, for example, thumbwheel select switches or a keyboard). Motor control 34 provides an RPM signal to computer 36 which represent the RPM (as sensed by RPM sensor 38), and a CURRENT signal which represents the drive current level being supplied by motor control 34 to motor 28. Based upon the RPM and CURRENT signals from motor control 34, computer 36 computes the flow rate of blood flow from centrifugal pump 16, and displays that computed flow rate on flow rate display 42.

The present invention takes advantage of the fact that at a constant speed of rotation and a constant viscosity, the torque required to drive centrifugal pump 16 is directly related to the flow produced by pump 16. In the embodiment shown in FIG. 1, the fact that the torque produced by a permanent magnet direct current motor 28 is directly related to the current required by that motor is also used. In other words, the CURRENT signal provided by motor control 34 to computer 36 is a signal which is representative of motor torque. The RPM signal which represents the motor speed of rotation, together with the current signal representative of motor torque, provide information which makes it possible to determine the flow rate provided that a value for viscosity is known. An approximate flow rate can be obtained simply by using an average viscosity value which is either stored in memory of computer 36 or which is entered through a data input device (not shown) by the operator.

In the embodiments shown in FIG. 1, calibration of the flowmeter of viscosity is achieved in a simple fashion. To calibrate the flow meter, the operator sets the desired RPM level and observes a flow rate as displayed by flow rate display 42. The operator then clamps outlet line 12, which reduces the flow to zero and presses ZERO SET pushbutton switch 44. Computer 36 then monitors the motor current (torque). A highly viscous fluid will cause a higher motor torque than a non-viscous fluid or one with lower viscosity. The level of motor current at zero flow is used to calibrate the flow measurement for viscosity. Computer 36 stores the viscosity calibration factor determined during calibration, and uses that viscosity factor in subsequent computations of flow rate. Line 12 is then unclamped and regular operation of system 10 continues. Should the viscosity change during use of system 10, the operator may recalibrate simply by clamping outlet line 12, reducing flow to zero and depressing zero set switch 44 again.

Figure 2:
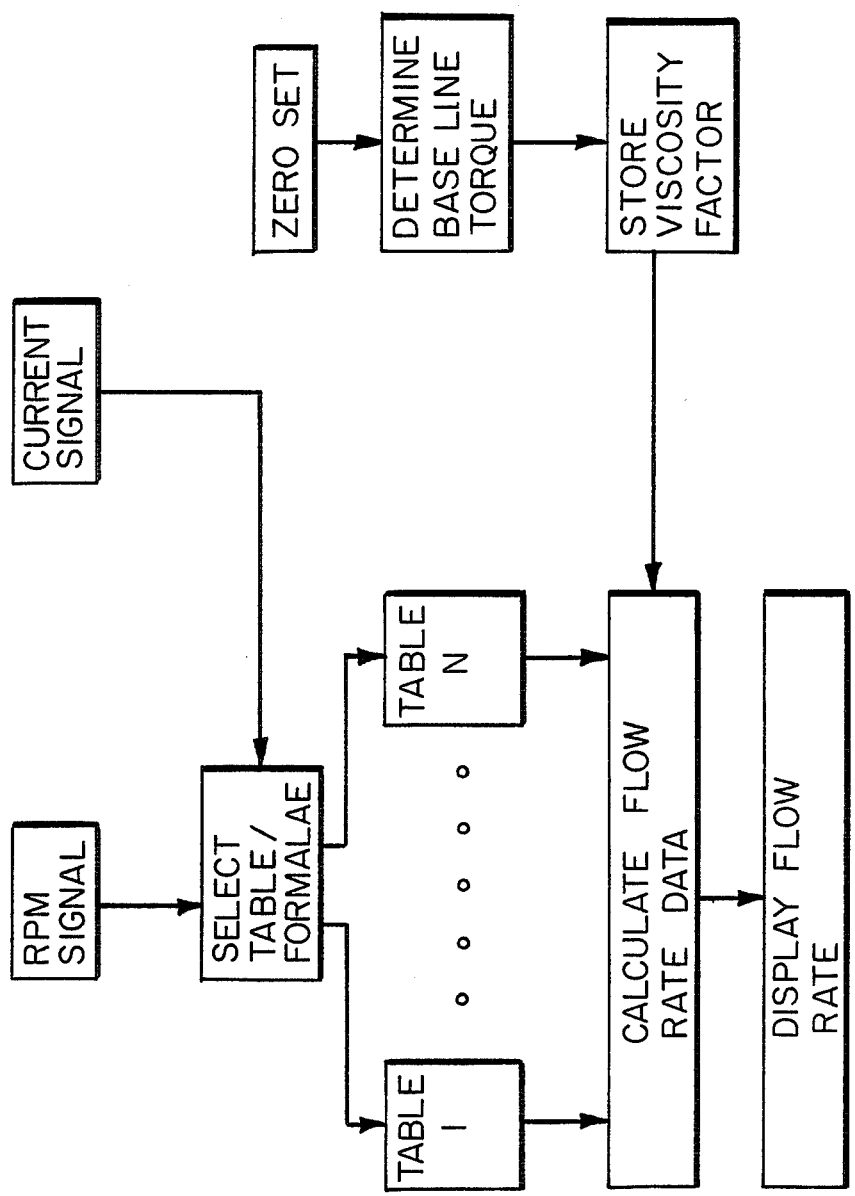
FIG. 2 shows a flow diagram of a preferred embodiment of the method of the present invention.

FIG. 2 shows a flow chart illustrating the steps performed by computer 36 in one embodiment of the present invention. As shown in FIG. 2, RPM and motor current values are supplied to computer 36 by motor control 34. These values are periodically sampled by computer 36. Utilizing the RPM value, one of a distinct set of tables and/or formulae which relate motor current to flow rate is selected. The selected table/formula and the motor current are used, together with the viscosity factor produced during calibration, to generate flow rate data. Based upon that flow rate data, computer 36 provides an output to flow rate display 42.

To verify that a table of values may be used to derive flow from motor torque and motor RPM, we conducted the following experiment:

A DC motor with both a torque display and a RPM measurement display was set up to pump water (using a centrifugal pump) from a reservoir through a float-type flowmeter and back to the same reservoir. Torque vs. flow data was taken at increments of 500 RPM between 2000 and 3500 RPM.

We observed that torque T increased linearly with flow at a constant RPM and could be fitted with a family of equations of the form $F = aT + b$. The data for the determination of the constant b was determined by observing the torque at zero flow for the several points of RPM.

We then used regression analysis to determine the best form for fitting the data for coefficient a. TABLE 1 shows the values of a and b for different RPM.

TABLE 1

| RPM | a | b |
|---|---|---|
| 1,000 | 4.580645 | −9.316129 |
| 2,000 | 2.676722 | −13.190987 |
| 2,500 | 2.171157 | −15.685156 |
| 3,000 | 2.022627 | −19.619783 |
| 3,500 | 1.764092 | −21.579332 |

Comparison of a linear plot of $F = aT + b$ gave a correlation of coefficient of approximately 0.99.

TABLE 2 gives the raw data used for calculating the constants b and multiplying factors a of the family of equations and comparing calculated and actual flow. The errors shown in TABLE 2 are relatively small, and the variability of plus and minus errors is believed to reflect inaccuracies in the experimental measurements.

TABLE 2

| RPM | Torque | Actual Flow | a | b | Calculated Flow (F) | Error |
|---|---|---|---|---|---|---|
| 1,000 | 2.0 | 0 | 4.580645 | −9.316129 | −.154839 | −.15 |
|  | 2.6 | 2 | 4.580645 | −9.316129 | 2.593548 | .59 |
|  | 2.7 | 3 | 4.580645 | −9.316129 | 3.051613 | .05 |
|  | 2.8 | 4 | 4.580645 | −9.316129 | 3.509677 | −.49 |
| 2,000 | 5.0 | 0 | 2.676722 | −13.190987 | .192623 | .19 |
|  | 5.8 | 2 | 2.676722 | −13.190987 | 2.334001 | .33 |
|  | 6.0 | 3 | 2.676722 | −13.190987 | 2.869345 | −.13 |
|  | 6.2 | 4 | 2.676722 | −13.190987 | 3.404689 | −.60 |
|  | 6.9 | 5 | 2.676722 | −13.190987 | 5.278395 | .28 |
|  | 7.2 | 6 | 2.676772 | −13.190987 | 6.081411 | .08 |
|  | 7.5 | 7 | 2.676722 | −13.190987 | 6.884428 | −.12 |
|  | 8.0 | 8 | 2.676722 | −13.190987 | 8.222789 | .22 |
| 2,500 | 7.3 | 0 | 2.171157 | −15.685156 | .164290 | .16 |
|  | 7.8 | 1 | 2.171157 | −15.685156 | 1.249869 | .25 |
|  | 8.2 | 2 | 2.171157 | −15.685156 | 2.118331 | .12 |
|  | 8.4 | 3 | 2.171157 | −15.685156 | 2.552563 | −.45 |
|  | 9.2 | 4 | 2.171157 | −15.685156 | 4.289488 | .29 |
|  | 9.5 | 5 | 2.171157 | −15.685156 | 4.940836 | −.06 |
|  | 10.0 | 6 | 2.171157 | −15.685156 | 6.026414 | .03 |
|  | 10.3 | 7 | 2.171157 | −15.685156 | 6.677761 | −.32 |
|  | 11.0 | 8 | 2.171157 | −15.685156 | 8.197571 | .20 |
| 3,000 | 9.6 | 0 | 2.022627 | −19.619783 | −.202564 | −.20 |
|  | 10.2 | 1 | 2.022627 | −19.619783 | 1.011012 | .01 |
|  | 10.9 | 2 | 2.022627 | −19.619783 | 2.426851 | .43 |
|  | 11.1 | 3 | 2.022627 | −19.619783 | 2.831377 | −.17 |
|  | 11.8 | 4 | 2.022627 | −19.619783 | 4.247216 | .25 |
|  | 12.0 | 5 | 2.022627 | −19.619783 | 4.651741 | −.35 |
|  | 12.8 | 6 | 2.022627 | −19.619783 | 6.269843 | .27 |
|  | 13.1 | 7 | 2.022627 | −19.619783 | 6.876631 | −.12 |
|  | 13.6 | 8 | 2.022627 | −19.619783 | 7.887944 | −.11 |
| 3,500 | 12.3 | 0 | 1.764092 | −21.579332 | .119000 | .12 |
|  | 12.8 | 1 | 1.764092 | −21.579332 | 1.001046 | .00 |
|  | 13.4 | 2 | 1.764092 | −21.579332 | 2.059501 | .06 |
|  | 14.0 | 3 | 1.764092 | −21.579332 | 3.117956 | .12 |
|  | 14.4 | 4 | 1.764092 | −21.579332 | 3.823593 | −.18 |
|  | 15.0 | 5 | 1.764092 | −21.579332 | 4.882048 | −.12 |
|  | 15.6 | 6 | 1.764092 | −21.579332 | 5.940503 | −.06 |
|  | 16.0 | 7 | 1.764092 | −21.579332 | 6.646140 | −.35 |
|  | 17.0 | 8 | 1.764092 | −21.579332 | 8.410232 | −.41 |

All of the measurements and calculations reflected in TABLE 2 are for a single viscosity. As described previously, a viscosity factor is preferably derived during calibration by measuring torque at a known RPM under zero flow conditions. As shown in TABLE 2, the torque will be know under those conditions for a given viscosity and the viscosity factor can then be calculated and stored for a later use to modify the measured values of T used in the selected formula of the form $F = aT + b$.

The method and system of the present invention provide a simple, yet very effective measurement of fluid flow in a centrifugal pump system, without requiring a separate flow measuring transducer. This simplifies the set up of the system, since the operator is not required to place the transducer on the outlet line. In addition, because the system merely makes use of signals which are used for other purposes, the flow measurement is not sensitive to electromagnetic radiation.

Although the present invention has been described with reference to preferred embodiments, workers skilled in the art will recognize that changes may be made in form and detail without departing form the spirit and scope of the invention.

What is claimed is:

1. A method of indirectly and noninvasively measuring blood flow in an outlet line connected to a motor driven centrifugal blood pump of a type having an inlet, and outlet connected to the outlet line, a housing, and an impeller which is rotated by the motor to pump blood from the inlet to the outlet, the method comprising:

sensing a first parameter to provide a first signal representative of pump impeller RPM;

sensing a second parameter to provide a second signal representative of motor torque;

computing a blood flow rate in the outlet line as a function of the first and second signals; and displaying a representation of the blood flow in the outlet line.

2. The method of claim 1 and further comprising:

determining a viscosity factor representative of viscosity of the blood; and wherein the computing of a blood flow rate is a function of the viscosity factor.

3. A method of indirectly and noninvasively measuring blood flow from a motor driven centrifugal blood pump, the method comprising:

sensing a first parameter to provide a first signal representative of pump RPM;

sensing a second parameter to provide a second signal representative of motor torque;

causing the pump to operate at a selected RPM;

clamping an outlet line from the pump to reduce blood flow to zero;

sensing the second parameter while the blood flow is zero and the pump is operating;

computing a viscosity factor representative of viscosity of the blood based upon the second signal as produced while the blood flow is zero and the pump is operating; and computing a blood flow rate as a function of the first and second signals and the viscosity factor.

4. The method of claim 1 wherein a motor which drives the pump is a DC electric motor and wherein the second parameter is a DC drive current to the DC electric motor.

5. The method of claim 1 wherein computing a blood flow rate comprises:

storing a plurality of RPM dependent tables which relate motor torque and blood flow rate;

selecting one of the tables based upon the first signal; and determining a blood flow rate based upon the table selected and the second signal.

6. In a centrifugal blood pump system which includes a centrifugal blood pump having an inlet, an outlet, a housing and an impeller; a motor which causes the impeller to rotate; and means for controlling the motor to produce a selected RPM of the impeller; the improvement comprising:

means for producing a first signal representative of RPM;

means for producing second signal representative of motor torque;

means for producing a third signal representative of blood flow rate from the outlet as a function of the first and second signals; and means for displaying a representation of the blood flow rate from the outlet as a function of the third signal.

7. The invention of claim 6 and further comprising:

means for storing a viscosity factor; and wherein the means for producing the third signal uses the viscosity factor.

* * * * *